United States Patent
Sunwoo et al.

(10) Patent No.: US 11,922,622 B2
(45) Date of Patent: Mar. 5, 2024

(54) CONVOLUTIONAL NEURAL NETWORK BASED BREAST IMAGE ANALYSIS METHOD USING FOUR-CHANNEL INPUTS AND SYSTEM THEREFOR

(71) Applicant: AJOU UNIVERSITY INDUSTRY-ACADEMIC COOPERATION FOUNDATION, Suwon-si (KR)

(72) Inventors: Myung Hoon Sunwoo, Seoul (KR); Ji Hoon Bae, Asan-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 481 days.

(21) Appl. No.: 17/277,443

(22) PCT Filed: Aug. 22, 2019

(86) PCT No.: PCT/KR2019/010690
§ 371 (c)(1),
(2) Date: Mar. 18, 2021

(87) PCT Pub. No.: WO2020/060046
PCT Pub. Date: Mar. 26, 2020

(65) Prior Publication Data
US 2022/0036544 A1    Feb. 3, 2022

(30) Foreign Application Priority Data
Sep. 20, 2018  (KR) .................. 10-2018-0113030

(51) Int. Cl.
G16H 30/20    (2018.01)
A61B 6/00    (2006.01)
(Continued)

(52) U.S. Cl.
CPC ............ *G06T 7/0012* (2013.01); *A61B 6/502* (2013.01); *G06N 3/08* (2013.01); *G06N 5/04* (2013.01);
(Continued)

(58) Field of Classification Search
CPC ...... A61B 6/502; A61B 6/5217; G06N 3/045; G06N 3/08; G06N 5/04; G06T 1/20;
(Continued)

(56) References Cited

U.S. PATENT DOCUMENTS 6,018,728 A * 1/2000 Spence .................. G06V 10/25
706/20
6,324,532 B1 * 11/2001 Spence ............. G06F 18/24155
706/19

(Continued)

FOREIGN PATENT DOCUMENTS

KR    10-2005-0043869 A    5/2005
KR    10-2015-0108701 A    9/2015
(Continued)

OTHER PUBLICATIONS

Gustavo Carneiro, "Deep Learning Models for Classifying Mammogram Exams Containing Unregistered Multi-View Images and Segmentation Maps of Lesions," Jan. 27, 2017, Deep Learning for Medical Image Analysis, 2017, pp. 321-330.*
(Continued)

*Primary Examiner* — Omar S Ismail
(74) *Attorney, Agent, or Firm* — Sughrue Mion, PLLC

(57) ABSTRACT

The present invention relates to a breast image analysis method with four mammogram images which are input to a convolutional neural network as one input and a system therefor and the system includes an image receiving unit which receives four mammogram images; an image size adjusting unit which adjusts a size of a mammogram image
(Continued)

received from the image receiving unit; a preprocessing unit which performs preprocessing on the mammogram image adjusted by the image size adjusting unit; a convolutional neural network (CNN)-based CNN learning unit which generates learning information by learning the mammogram image preprocessed by the preprocessing unit; and a CNN inference unit which receives the learning information learned from the CNN learning unit and a mammogram image to be classified from the image receiving unit to diagnose a breast abnormality.

7 Claims, 15 Drawing Sheets

(51) Int. Cl.
*G06N 3/08* (2023.01)
*G06N 5/04* (2023.01)
*G06T 3/40* (2006.01)
*G06T 7/00* (2017.01)

(52) U.S. Cl.
CPC ............... *G06T 3/40* (2013.01); *G16H 30/20* (2018.01); *G06T 2207/20081* (2013.01); *G06T 2207/20084* (2013.01); *G06T 2207/30068* (2013.01)

(58) Field of Classification Search
CPC . G06T 2207/10116; G06T 2207/20081; G06T 2207/20084; G06T 2207/30068; G06T 3/40; G06T 7/0012; G16H 30/20; G16H 30/40; G16H 50/20; G16H 50/70
See application file for complete search history.

(56) References Cited

U.S. PATENT DOCUMENTS

| | | | | |
|---|---|---|---|---|
| 2002/0012458 | A1* | 1/2002 | Wang | G16H 15/00 382/132 |
| 2002/0076091 | A1* | 6/2002 | Wang | G06T 7/0012 382/132 |
| 2002/0097902 | A1* | 7/2002 | Roehrig | G06F 3/0481 382/132 |
| 2013/0051676 | A1* | 2/2013 | Wehnes | G06T 5/10 382/190 |
| 2013/0251207 | A1* | 9/2013 | Mukhopadhyay | G06V 20/69 382/103 |
| 2015/0196265 | A1* | 7/2015 | Suzuki | G06V 10/776 378/37 |
| 2017/0249739 | A1* | 8/2017 | Kallenberg | G06F 18/24143 |
| 2019/0189266 | A1* | 6/2019 | Stoval, III | G06N 3/08 |
| 2019/0189267 | A1* | 6/2019 | Stoval, III | G06N 20/00 |
| 2019/0189268 | A1* | 6/2019 | Stoval, III | G16H 50/70 |

FOREIGN PATENT DOCUMENTS

| | | |
|---|---|---|
| KR | 10-1857624 B1 | 5/2018 |
| KR | 10-1887760 B1 | 8/2018 |

OTHER PUBLICATIONS

J. Dheeba, "Computer-aided detection of breast cancer on mammograms: A swarm intelligence optimized wavelet neural network approach," Feb. 6, 2014, Journal of Biomedical Informatics 49 (2014), pp. 45-50.*
Pengcheng Xi, "Abnormality Detection in Mammography using Deep Convolutional Neural Networks", Aug. 19, 2018,2018 IEEE International Symposium on Medical Measurements and Applications (MeMeA), pp. 1-5.*
Maxine Tan, "Assessment of a Four-View Mammographic Image Feature Based Fusion Model to Predict Near-Term Breast Cancer Risk",Apr. 8, 2015, Annals of Biomedical Engineering, vol. 43, No. 10, Oct. 2015, pp. 2416-2423.*
Shuyue Guan, "Breast Cancer Detection Using Transfer Learning in Convolutional Neural Networks", Sep. 11, 2018, 2017 IEEE Applied Imagery Pattern Recognition Workshop (AIPR), p. 1-6.*
Krzysztof J. Geras, "High-Resolution Breast Cancer Screening with Multi-View Deep Convolutional Neural Networks",Jun. 28, 2018, Computer Vision and Pattern Recognition, arXiv:1703.07047 Search, pp. 2-8.*
Sergio Koodi Kinoshita, "Content-based Retrieval of Mammograms Using Visual Features Related to Breast Density Patterns," Feb. 22, 2007, Journal of Digital Imaging, vol. 20, No. 2 Jun. 2007, pp. 172-181.*
Sarah S. Aboutalib, "Deep Learning to Distinguish Recalled but Benign Mammography Images in Breast Cancer Screening," Dec. 3, 2018, Precision Medicine and Imaging, Clin Cancer Res; 24(23) Dec. 1, 2018, pp. 5902-5904.*
Raúl Ramos-Pollan, "Discovering Mammography-based Machine Learning Classifiers for Breast Cancer Diagnosis," Apr. 9, 2011,J Med Syst (2012) 36, pp. 2261-2264.*
Ricardo Thomaz, "Feature extraction using convolutional neural network for classifying breast density in mammographic images," Mar. 3, 2017, Proceedings of SPIE, pp. 1-6.*
Abdullah-Al Nahid, "Histopathological Breast-Image Classification Using Local and Frequency Domains by Convolutional Neural Network," Jan. 16, 2018, Information 2018, 9, 19, pp. 1-12.*
Gustavo Carneiro et al., "Unregistered Multiview Mammogram Analysis with Pre-trained Deep Learning Models", International Conference on Medical Image Computing and Computer-Assisted Intervention, 2015, pp. 652-660.
International Search Report of PCT/KR2019/010690 dated Dec. 9, 2019 [PCT/ISA/210].
Korean Office Action of KR10-2018-0113030 dated Aug. 21, 2019.
Written Opinion of PCT/KR2019/010690 dated Dec. 9, 2018.

* cited by examiner

[Fig. 1]
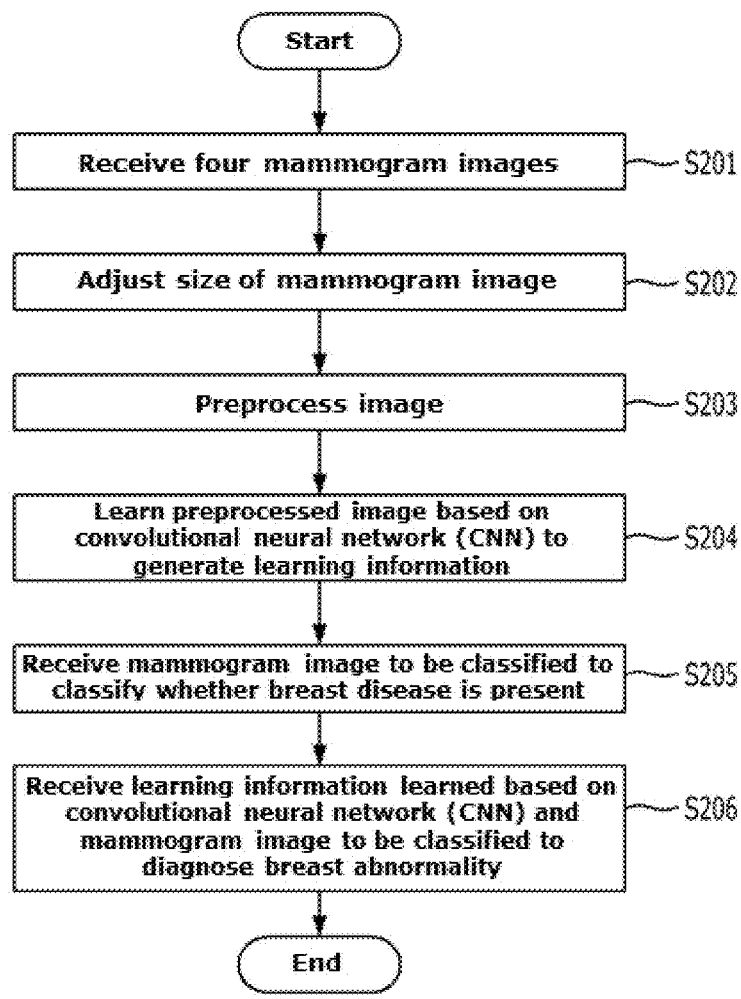

[Fig. 2]
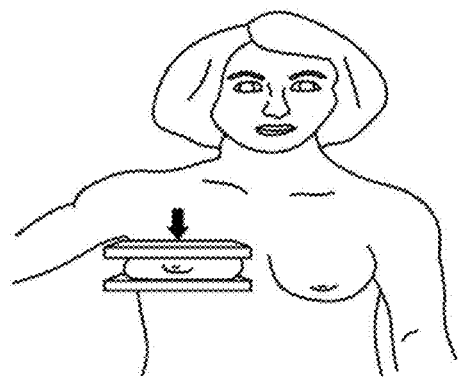
(a)
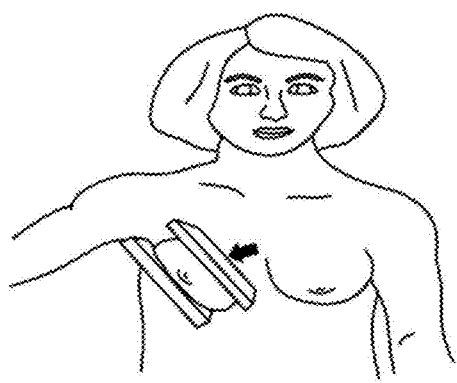
(b)

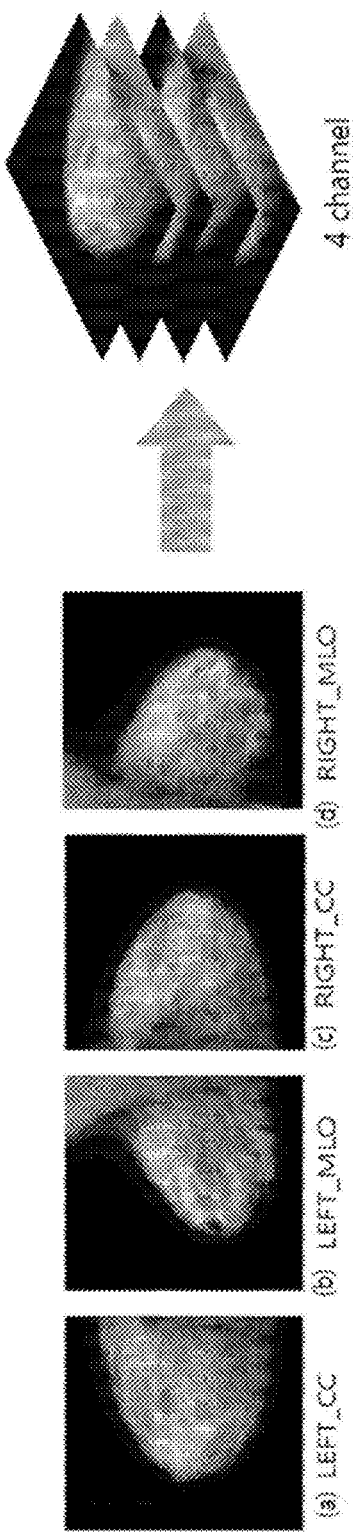
[Fig. 3]

[Fig. 4A]
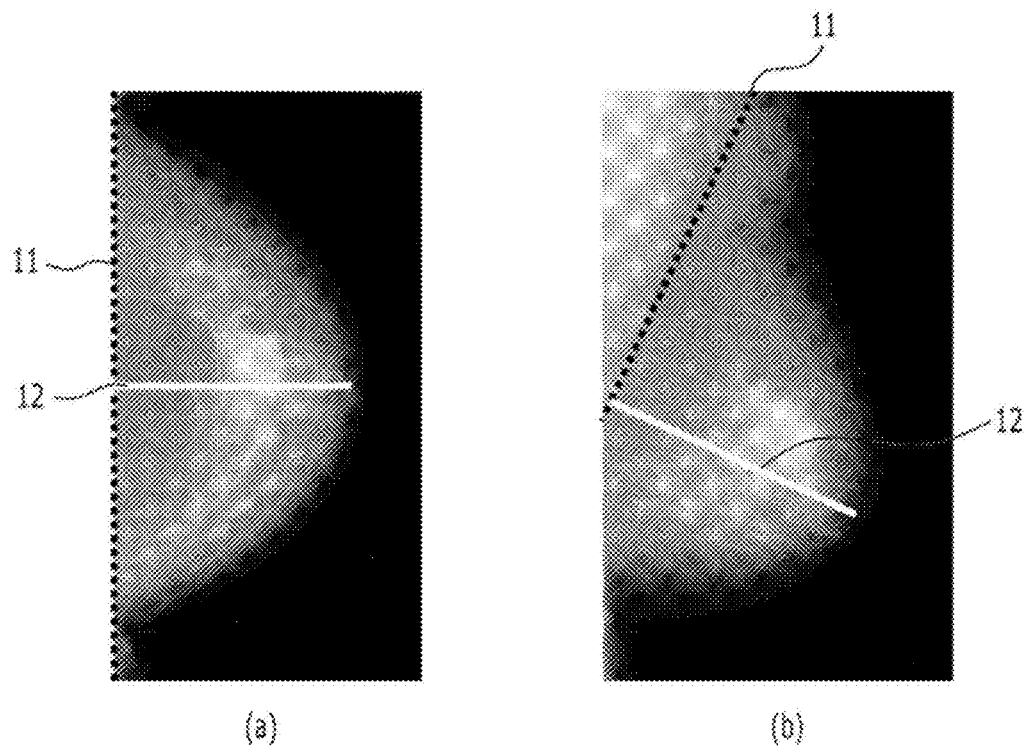

[Fig. 4B]
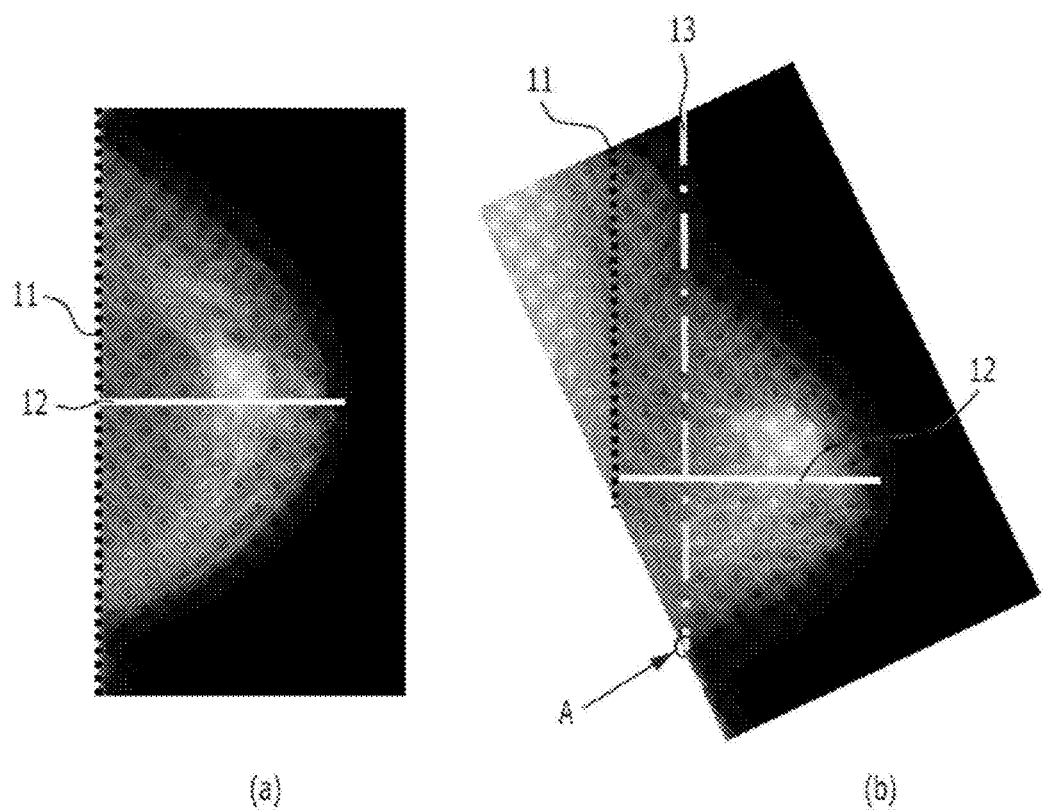

[Fig. 4C]
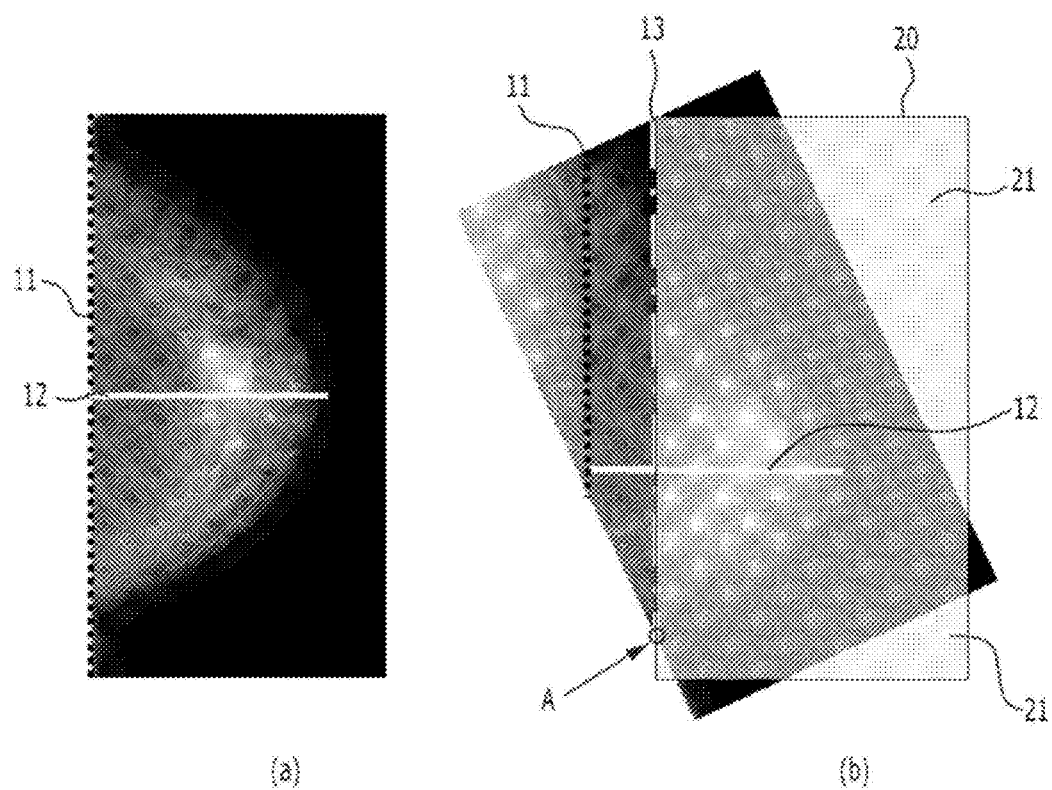

[Fig. 4D]
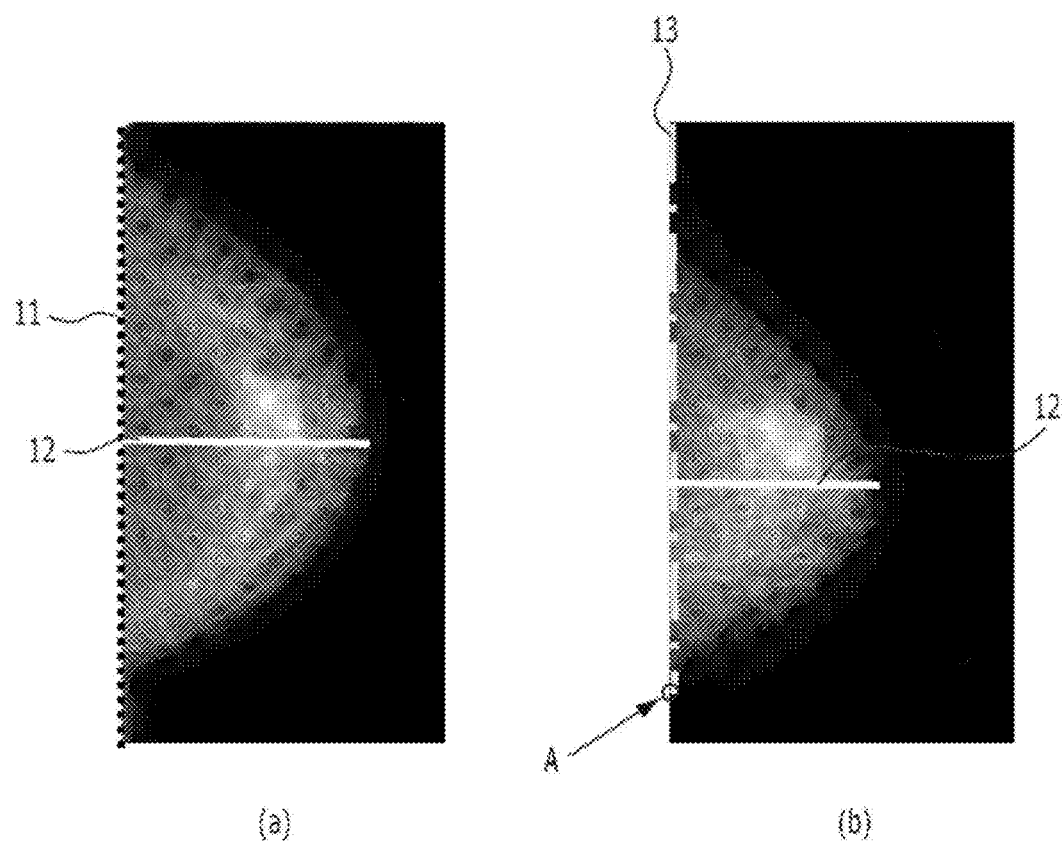

[Fig. 5]
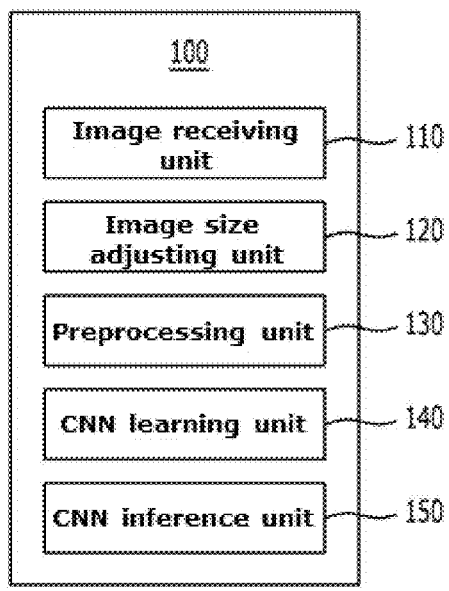
[Fig. 6]
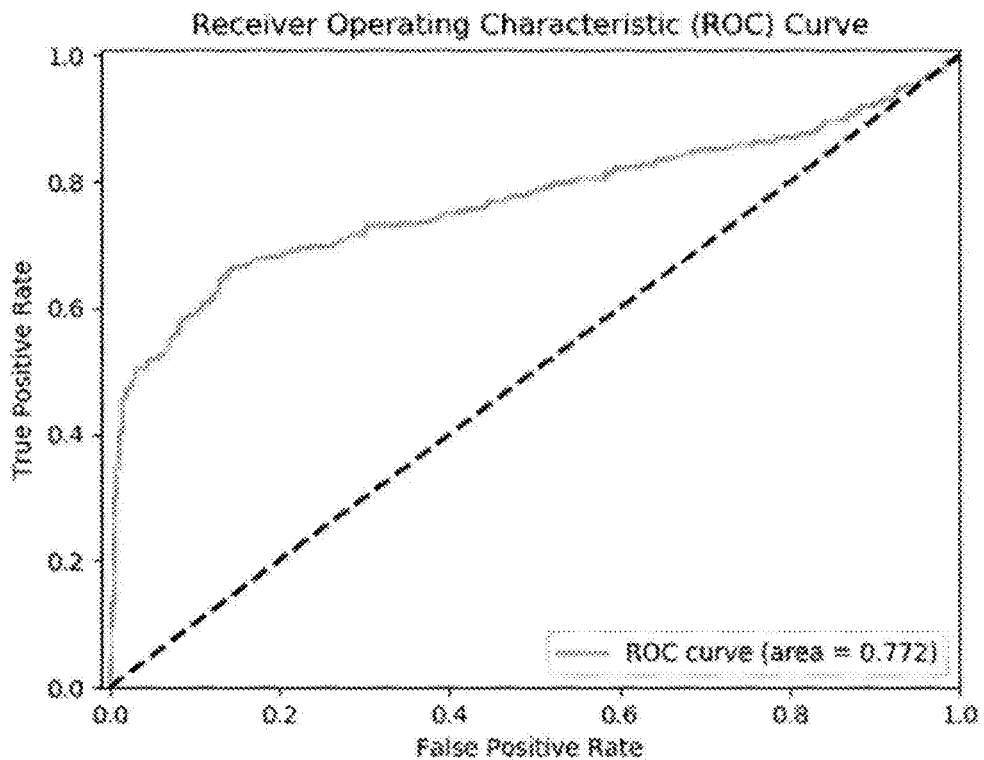

[Fig. 7]
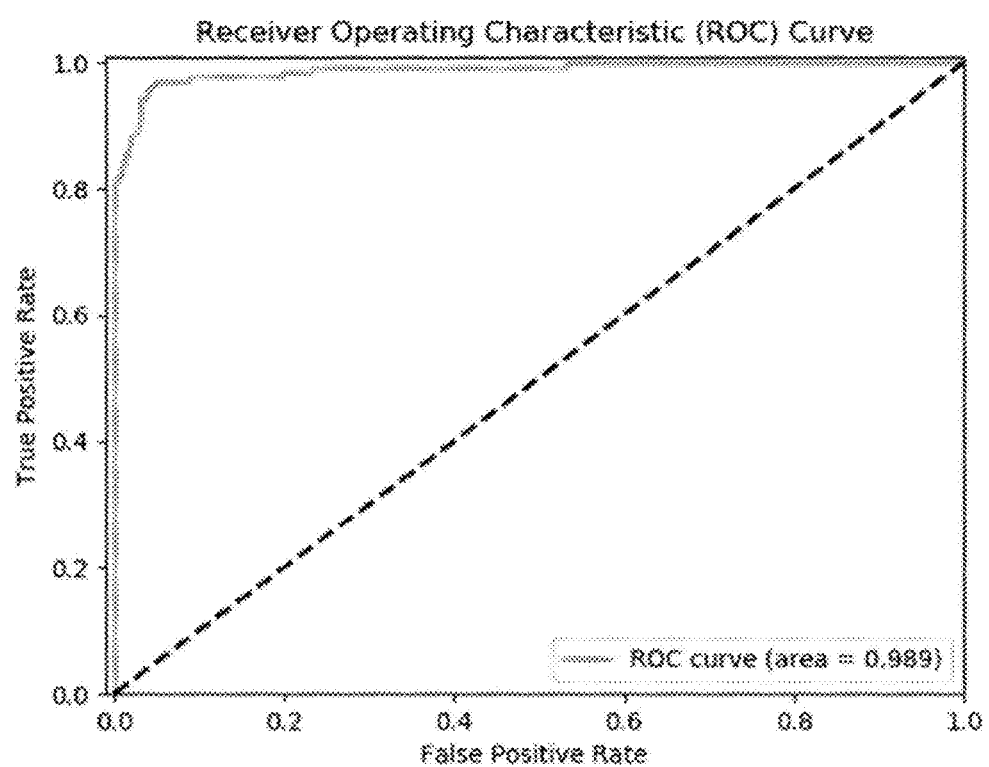

[Fig. 8]
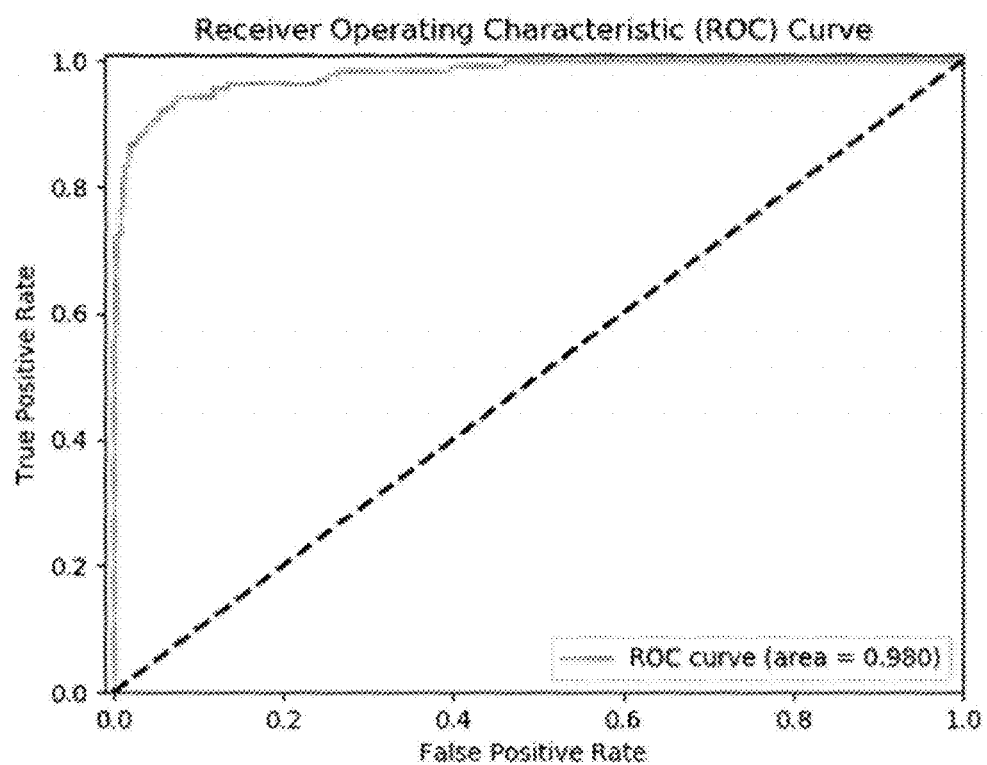

[Fig. 9]
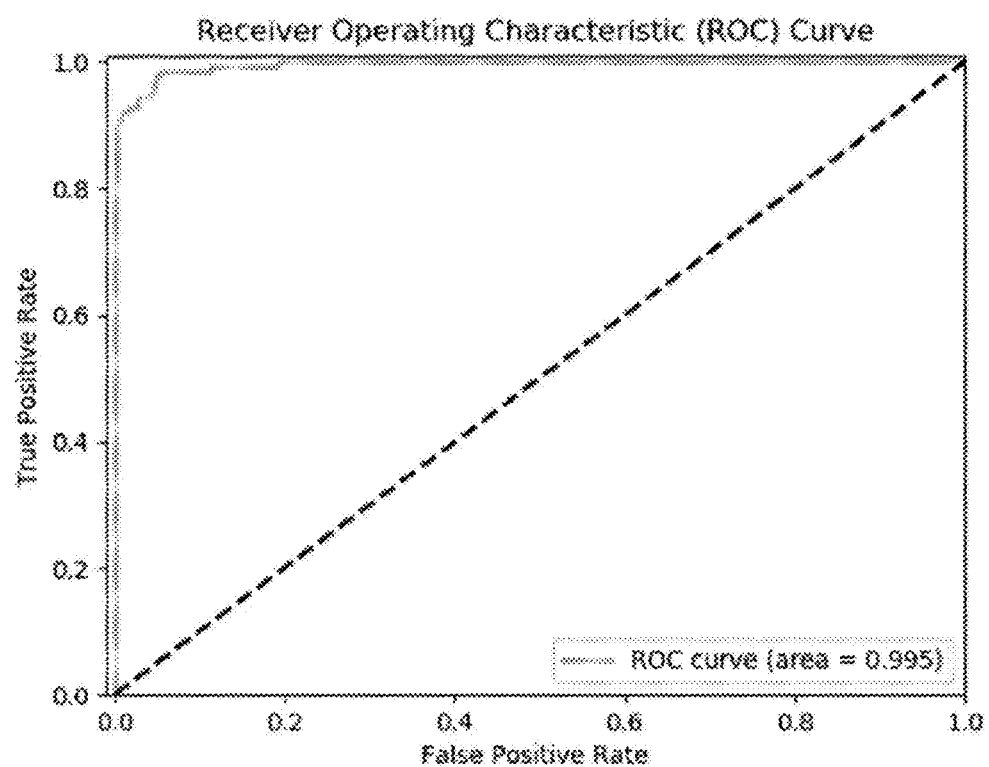

[Fig. 10]
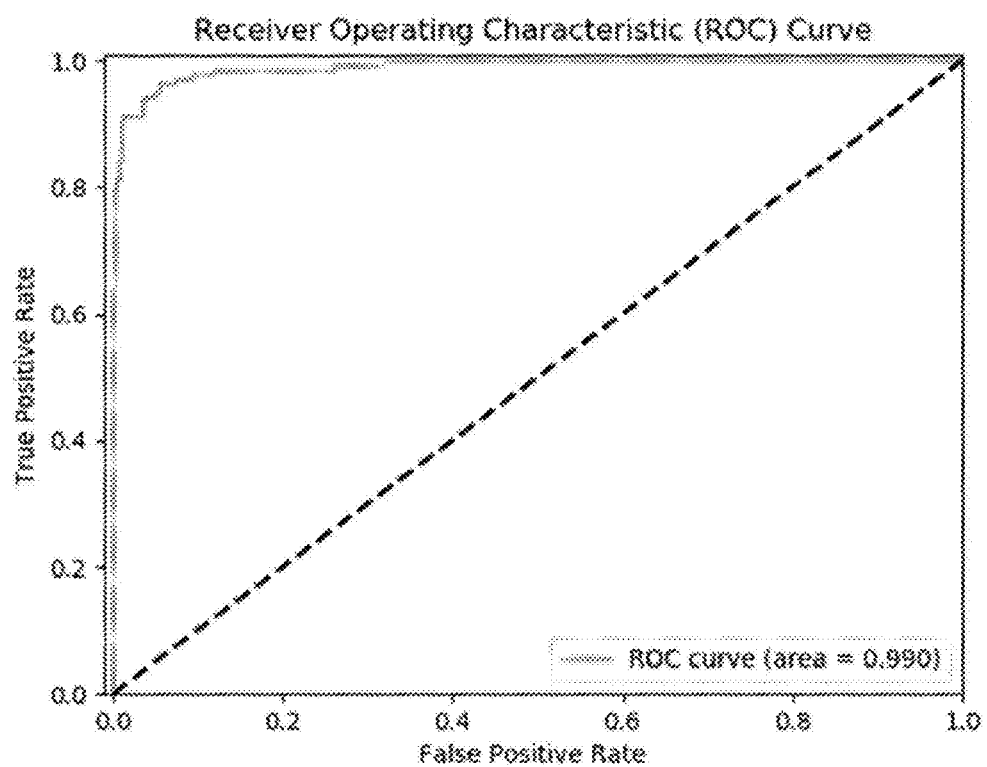

[Fig. 11]
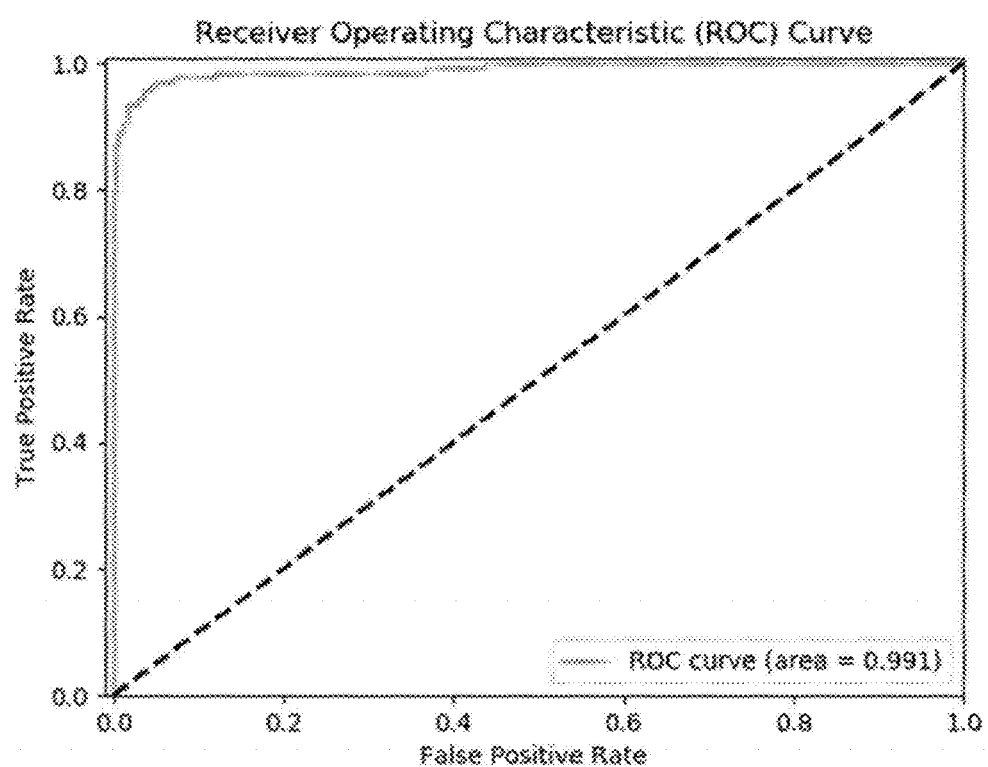

[Fig. 12]
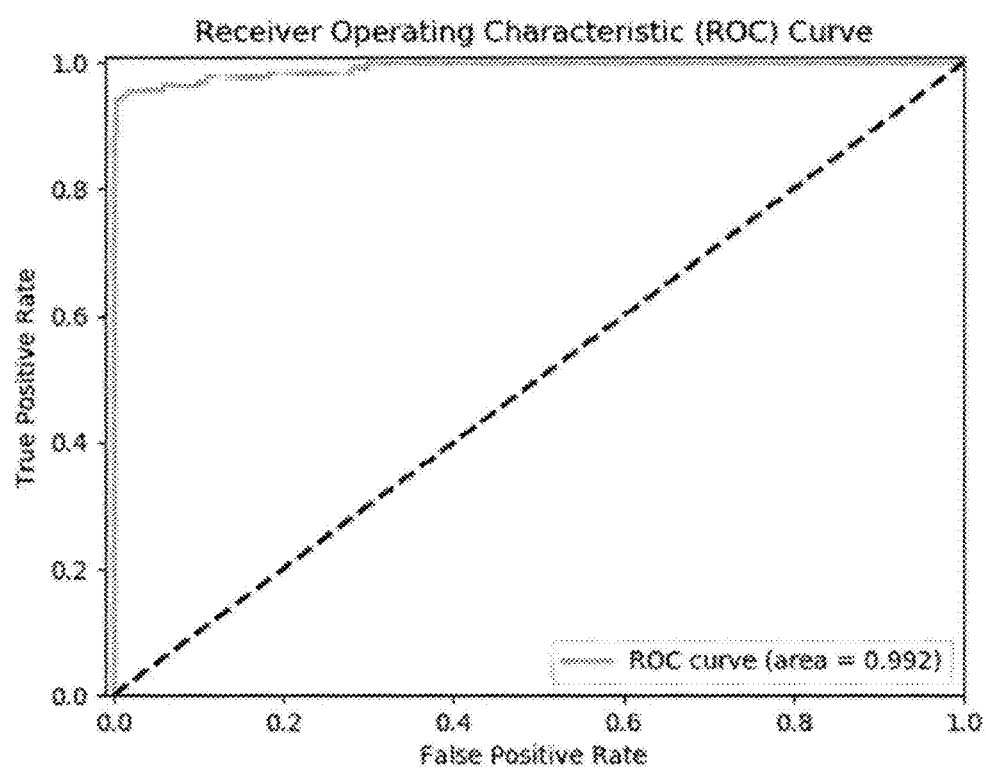

[Fig. 13]
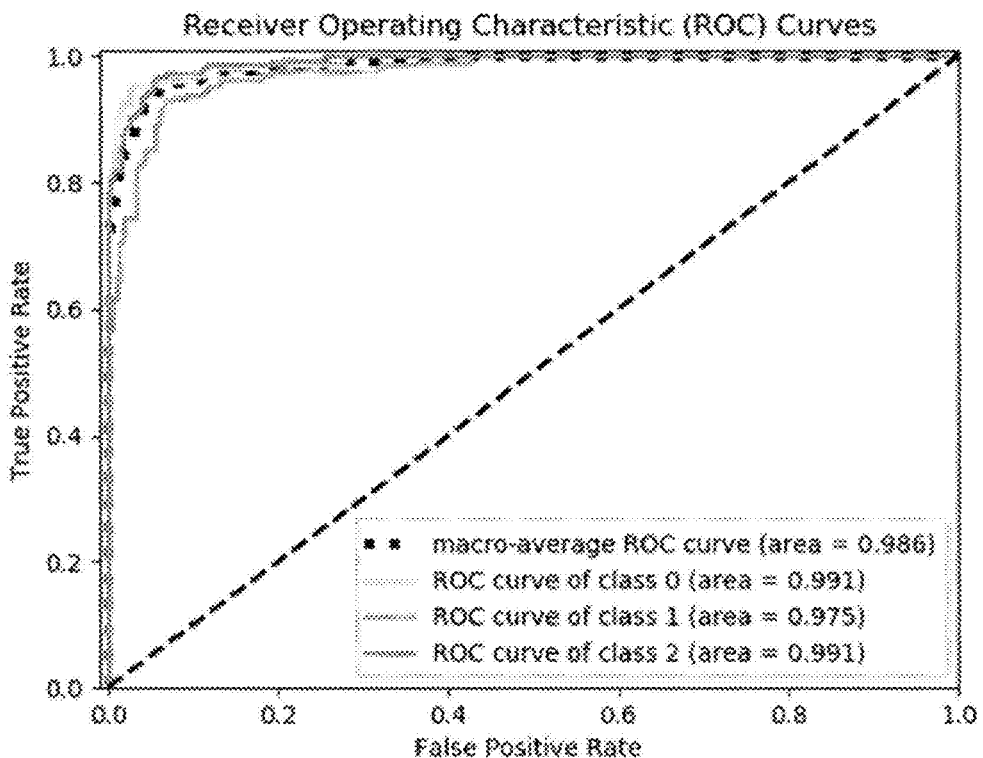
[Fig. 14]
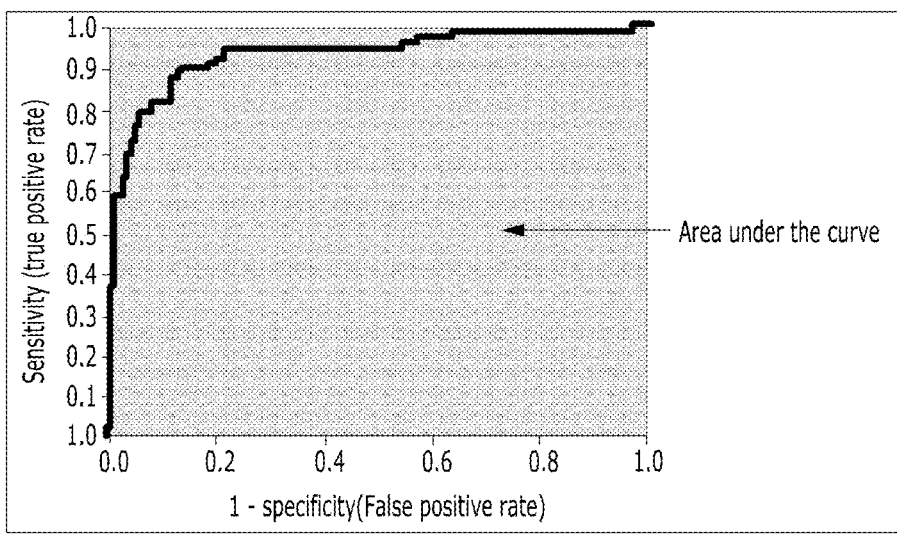

CONVOLUTIONAL NEURAL NETWORK BASED BREAST IMAGE ANALYSIS METHOD USING FOUR-CHANNEL INPUTS AND SYSTEM THEREFOR

CROSS REFERENCE TO RELATED APPLICATIONS

This application is a National Stage of International Application No. PCT/KR2019/010690 filed on Aug. 22, 2019, claiming priority based on Korean Patent Application No. 10-2018-0113030 filed on Sep. 20, 2018.

TECHNICAL FIELD

The present invention relates to a breast image analysis method with four mammogram images which are input to a convolutional neural network as one input and a system therefor.

BACKGROUND ART

According to the mammography, a specialist determines X-ray photographs with naked eyes so that misdiagnosis may occur depending on the experience and the skill of a doctor who diagnoses the image, which may cause unnecessary additional tests. Indeed, the sensitivity and the specificity of an experienced radiologist are 62 to 87% and 75 to 91%, respectively.

In order to solve this problem, in recent years, studies are being conducted to diagnose medical images using deep learning. Among the deep learning techniques, a convolutional neural network of the related art uses only one image as an input, so that there is a limitation in that an analysis performance is not high.

DISCLOSURE

Technical Problem

The present invention has been made an effort to overcome the above-mentioned limitation and an object of the present invention is to provide a convolutional neural network-based breast image analysis method using four-channel inputs and a system therefor.

Technical objects of the present invention are not limited to the aforementioned technical objects and other technical objects which are not mentioned will be apparently appreciated by those skilled in the art from the following description.

Technical Solution

A breast image analysis system according to an exemplary embodiment of the present invention includes an image receiving unit which receives four mammogram images; an image size adjusting unit which adjusts a size of a mammogram image received from the image receiving unit; a preprocessing unit which performs preprocessing on the mammogram image adjusted by the image size adjusting unit; a convolutional neural network (CNN)-based CNN learning unit which generates learning information by learning the mammogram image preprocessed by the preprocessing unit; and a CNN inference unit which receives the learning information learned from the CNN learning unit and a mammogram image to be classified from the image receiving unit to diagnose a breast abnormality.

The mammogram image to be classified which is received by the CNN inference unit according to the exemplary embodiment of the present invention may have a size which is adjusted by the size adjusting unit and the preprocessing may be performed on the mammogram image in the preprocessing unit.

Four mammogram images according to an exemplary embodiment of the present invention include a right craniocaudal (CC) view, a left craniocaudal (CC) view, a right mediolateral oblique (MLO) view, and a left mediolateral oblique (MLO) view.

The image size adjusting unit according to the exemplary embodiment of the present invention may change an angle with respect to the mediolateral oblique view image and cut only a breast side image with respect to a pectoral muscle parallel line which is parallel to a pectoral muscle line represented in the mediolateral oblique view image and has a predetermined interval toward a nipple direction from the pectoral muscle line to be adjusted in the form of a craniocaudal (CC) view.

The pectoral muscle line according to the exemplary embodiment of the present invention may pass through a point at which a breast in a lower side of a nipple meets at the boundary of the mediolateral oblique view image.

A breast image analysis method according to an exemplary embodiment of the present invention may include (a) a step of receiving four mammogram images, (b) a step of adjusting sizes of the received mammogram images; (c) a step of preprocessing the adjusted mammogram images; (d) a step of generating learning information by learning the preprocessed mammogram images based on a convolutional neural network (CNN); (e) a step of receiving a mammogram image to be classified to classify whether a breast disease is present; and (f) a step of receiving the learning information learned based on the convolutional neural network (CNN) and the mammogram image to be classified to diagnose a breast abnormality.

The step (e) of receiving a mammogram image to be classified according to the exemplary embodiment of the present invention may further include a step of adjusting a size of an image and a step of performing preprocessing on the adjusted mammogram image.

In the step (b) of adjusting a size of the received mammogram image according to the exemplary embodiment of the present invention, an angle with respect to the mediolateral oblique view image is adjusted and only a breast side image is cut with respect to a pectoral muscle parallel line which is parallel to a pectoral muscle line represented in the mediolateral oblique view image and has a predetermined interval toward a nipple direction from the pectoral muscle line to be adjusted in the form of a craniocaudal (CC) view.

Advantageous Effects

The convolutional neural network-based breast image analysis method using four-channel inputs according to an exemplary embodiment of the present invention and a system therefor comprehensively learn/analyze four images to increase a determination rate of a breast cancer as compared with the existing method.

Accordingly, a misdiagnosis rate of doctors is lowered and additional tests which are not necessary for patients may be prevented.

Further, according to the present invention, excellent performance may be provided from four-channel inputs regardless of the order of the images and even though there are three classes to be analyzed (normal, cancer, and benign) as well as two classes (negative and positive), the analysis performance is excellent.

The effects of the present invention are not limited to the technical effects mentioned above, and other effects which are not mentioned can be clearly understood by those skilled in the art from the following description

BRIEF DESCRIPTION OF DRAWINGS

FIG. 1 is a flowchart of a breast image analysis method according to an exemplary embodiment of the present invention.

FIG. 2 illustrates a method of acquiring a breast image according to an exemplary embodiment of the present invention.

FIG. 3 illustrates four mammogram images to be input to a convolutional neural network according to an exemplary embodiment of the present invention.

FIGS. 4A to 4D illustrate a method of adjusting a size of a mammogram image according to an exemplary embodiment of the present invention.

FIG. 5 is a block diagram of a breast image analysis system according to an exemplary embodiment of the present invention.

FIG. 6 is a graph illustrating an effect of a breast image analysis method using two channel inputs.

FIGS. 7 to 13 are graphs illustrating effects of a breast image analysis method according to an exemplary embodiment of the present invention and a system therefor.

FIG. 14 is a graph illustrating ROC curve.

BEST MODE

Those skilled in the art may make various modifications to the present invention and the present invention may have various embodiments thereof, and thus specific embodiments will be described in detail with reference to the drawings. However, this does not limit the present invention within specific exemplary embodiments, and it should be understood that the present invention covers all the modifications, equivalents and replacements within the spirit and technical scope of the present invention. In the description of respective drawings, similar reference numerals designate similar elements.

Terms such as first, second, A, or B may be used to describe various components but the components are not limited by the above terms. The above terms are used only to discriminate one component from the other component. For example, without departing from the scope of the present invention, a first component may be referred to as a second component, and similarly, a second component may be referred to as a first component. A term of and/or includes combination of a plurality of related elements or any one of the plurality of related elements.

It should be understood that, when it is described that an element is "coupled" or "connected" to another element, the element may be directly coupled or directly connected to the other element or coupled or connected to the other element through a third element. In contrast, when it is described that an element is "directly coupled" or "directly connected" to another element, it should be understood that no element is present therebetween.

Terms used in the present application are used only to describe a specific exemplary embodiment, but are not intended to limit the present invention. A singular form may include a plural form if there is no clearly opposite meaning in the context. In the present application, it should be understood that term "include" or "have" indicates that a feature, a number, a step, an operation, a component, a part or the combination those of described in the specification is present, but do not exclude a possibility of presence or addition of one or more other features, numbers, steps, operations, components, parts or combinations, in advance.

If it is not contrarily defined, all terms used herein including technological or scientific terms have the same meaning as those generally understood by a person with ordinary skill in the art. Terms defined in generally used dictionary shall be construed that they have meanings matching those in the context of a related art, and shall not be construed in ideal or excessively formal meanings unless they are clearly defined in the present application.

In the specification and the claim, unless explicitly described to the contrary, the word "comprise" and variations such as "comprises" or "comprising", will be understood to imply the inclusion of stated elements but not the exclusion of any other elements.

Hereinafter, exemplary embodiments according to the present invention will be described in detail with reference to accompanying drawings.

FIG. 1 is a flowchart of a breast image analysis method according to an exemplary embodiment of the present invention.

Referring to FIG. 1, the breast image analysis method may include (a) a step of receiving four mammogram images (S201), (b) a step of adjusting sizes of the received mammogram images (S202), (c) a step of preprocessing the adjusted mammogram images (S203), (d) a step of generating learning information by learning the preprocessed mammogram images based on a convolutional neural network (CNN) (S204), (e) a step of receiving a mammogram image to be classified to classify whether a breast disease is present (S205), and (f) a step of receiving the learning information learned based on the convolutional neural network (CNN) and the mammogram image to be classified to diagnose a breast abnormality (S206).

The step (S205) of receiving a mammogram image to be classified according to the exemplary embodiment of the present invention may further include a step of adjusting a size of the image and a step of preprocessing the adjusted mammogram image.

Breast images according to an exemplary embodiment of the present invention are a total of four mammogram images including a right craniocaudal (CC) view, a left craniocaudal (CC) view, a right mediolateral oblique (MLO) view, and a left mediolateral oblique (MLO) view.

FIG. 2 illustrates a method of acquiring a breast image according to an exemplary embodiment of the present invention.

The method of acquiring a breast image is generally performed by a breast X-ray exam such that a breast is located between a compression paddle and a film holder and the breast tissue is compressed to capture an X-ray image.

According to a method of acquiring craniocaudal (CC) views among four mammogram images, as illustrated in FIG. 2(a), a compression paddle and a film holder are located above the breast and below the breast to compress the breast and two craniocaudal views for a right side and a left side are acquired.

According to a method of acquiring mediolateral oblique (MLO) views, as illustrated in FIG. 2(b), the compression paddle and the film holder are disposed obliquely to the breast and the breast is compressed between the compression paddle and the film holder to acquire an X-ray image.

FIG. 3 illustrates four mammogram images to be input to a convolutional neural network according to an exemplary embodiment of the present invention.

Referring to FIG. 3, four mammogram images including a left craniocaudal (CC) view (a), a left mediolateral oblique (MLO) view (b), a right craniocaudal (CC) view (c), and a right mediolateral oblique (MLO) view (d) serve as inputs of the convolutional neural network (CNN).

A size of input data of a general convolutional neural network for a black and white image is (W, H, 1). In contrast, in the breast image analysis method according to the exemplary embodiment of the present invention, four channel inputs are used so that the size of the input data of the convolutional neural network may be (W, H, 4). Here, W is a horizontal size of an image pixel and H is a vertical size of an image pixel.

According to the exemplary embodiment of the present invention, the above-described four mammogram images serve as one input of the convolutional neural network so that the learning and the inference based on the convolutional neural network may be comprehensively determined.

In the meantime, the convolutional neural network (CNN) is specialized in two-dimensional image processing and has been mainly used for recognition problems. As a first basic key feature, there is a local receptive field so as to focus on extraction of a feature which expresses a part of an image and as a second basic key feature, weights representing the feature can be shared in the entire region of the image. Therefore, the convolutional neural network is one of deep learning algorithms which reduces a huge number of parameters and shares the feature regardless of the location of the image.

In the convolutional neural network, if a process of creating an upper layer by stacking one layer and reducing the number of nodes is repeated, the generalization is obtained as it goes to a higher layer. Hereinafter, general information about the convolutional neural network (CNN) will be omitted.

In the meantime, a data set to be learned using the convolutional neural network (CNN) may be distinguished from a data set for inferring a mammogram image using the convolutional neural network (CNN).

That is, with regard to the mammogram image included in the learning data set, a data set with a knowledge about whether a patient has a lesion or a progression of the lesion may be used. However, with regard to the mammogram image to be classified according to the exemplary embodiment of the present invention, a data set with no information about whether a patient has a lesion or a progression of the lesion may be used.

In the breast image analysis method according to the exemplary embodiment of the present invention, four different images are used as inputs so that preprocessing for the images is performed.

The preprocessing process may include the step of adjusting a size of the mammogram image (S202) and a preprocessing step (S203) of increasing a contrast of the black and white image.

FIGS. 4A to 4D illustrate a method of adjusting a size of a mammogram image according to an exemplary embodiment of the present invention. Between two images included in FIGS. 4A to 4D, the image (a) is a right craniocaudal (CC) view and the image (b) is a right mediolateral oblique (MLO) view.

The step (S202) of adjusting a size of the mammogram image will be described with reference to FIGS. 4A to 4D.

Referring to FIG. 4A, in the craniocaudal (CC) view image (a), a pectoral muscle line 11 is vertical in the image, but in the mediolateral oblique view image (b), the pectoral muscle line 11 is oblique in the image so that the positions of the breast do not match.

Accordingly, in order to match the positions of the breast, as illustrated in FIG. 4B, in the mediolateral oblique view image (b), the pectoral muscle line 11 is leaned to be perpendicular to a pectoral muscle-nipple line 12 as in the craniocaudal (CC) view image (a).

In the right breast image, the pectoral muscle line is rotated by approximately 45 degrees in a counterclockwise direction, and in the left breast image, the pectoral muscle line is rotated by approximately 45 degrees in a clockwise direction.

Further, a pectoral muscle parallel line 13 which is parallel to the pectoral muscle line 11 and has a predetermined interval toward the nipple direction from the pectoral muscle line 11 is disposed in the mediolateral oblique view image (b).

The pectoral muscle parallel line 13 is perpendicular to the pectoral muscle-nipple line 12 and passes through a point A at which a breast on a lower side of the nipple meets at the boundary of the mediolateral oblique view image.

Referring to FIG. 4C, only an image in which the breast is disposed with respect to the pectoral muscle parallel line 13 is cut to be adjusted in the form of a craniocaudal (CC) view.

The cutting area 20 has the same size as the craniocaudal (CC) view and a blank part 21 in the cutting area which does not include an image is processed such that the image does not appear by setting a pixel value to be 0.

The image size is adjusted by the above-described method so that as illustrated in FIG. 4D, the positions of the breasts in different mammogram images match as much as possible. Therefore, the precision of the convolutional neural network learning and inference may be increased.

In the process (S203) of preprocessing a mammogram image, a contrast limited adaptive histogram equalization (CLAHE) algorithm which increases a contrast of the black and white image is applied. The CLAHE algorithm has a mechanism which divides an image into small blocks with a constant size and performs histogram equalization for every block to achieve equalization for the entire image. As the CLAHE algorithm, an algorithm of the related art is used and the detailed description of the CLAHE algorithm will be omitted below.

FIG. 5 is a block diagram of a breast image analysis system according to an exemplary embodiment of the present invention.

A breast image analysis system 100 according to an exemplary embodiment of the present invention may include an image receiving unit 110 which receives four mammogram images, an image size adjusting unit 120 which adjusts a size of a mammogram image received from the image receiving unit, a preprocessing unit 130 which performs preprocessing on the mammogram image adjusted by the image size adjusting unit, a convolutional neural network (CNN)-based CNN learning unit 140 which generates learning information by learning the mammogram image preprocessed by the preprocessing unit, and a CNN inference unit 150 which receives the learning information learned from the CNN learning unit and a mammogram image to be classified from the image receiving unit to diagnose a breast abnormality.

The mammogram image to be classified which is received by the CNN inference unit 150 according to the exemplary embodiment of the present invention may have an image size which is adjusted by the size adjusting unit 120 and the preprocessing may be performed on the mammogram image in the preprocessing unit 130.

The contents for the breast image analysis method may be applied to the description of the breast image analysis system according to the exemplary embodiment of the present invention in the same manner.

The effect of the breast image analysis method according to the exemplary embodiment of the present invention is represented by a receiver operating characteristic (ROC) curve and an area under the curve (AUC).

The ROC curve and the AUC are used to quantify how well the problem is classified into two categories. Two categories may be normal (negative) and abnormal (positive).

The ROC curve is represented using a sensitivity (true positive rate: TPR) and a specificity (true negative rate: TNR) in which the sensitivity is the number of data which is determined to be positive among real positive data and the specificity is the number of data which is determined to be negative among real negative data.

The sensitivity and the specificity basically have an inverse proportional relationship (trade-off relationship) in which when one is increased, the other is decreased. For example, with respect to a threshold T and data X, if it is assumed that "when X>T, it is positive and when X<T, it is negative", when the T value is reduced, it is represented that "the sensitivity is increased and the specificity is decreased" and when the T value is increased, it is represented that "the sensitivity is decreased and the specificity is increased".

The ROC curve graph expresses this relationship. That is, Referring to FIG. 14, the ROC curve graph indicates changes in the sensitivity and the specificity in accordance with the change of the T value and a vertical axis of the graph represents [sensitivity] and a horizontal axis represents [1−specificity]. Here, "1−specificity=1−TNR=FPR (false positive rate)".

The AUC is used to quantify the ROC curve and means a width of an area under the ROC curve. That is, the AUC means a value obtained by integrating the ROC curve with respect to T and may be represented as follows.

$$AUC = \int_{\infty}^{-\infty} TPR(T) FPR'(T) dT$$

A graph illustrating an effect of the breast image analysis method illustrated in FIGS. 6 to 17 will be described with reference to the above ROC curve.

FIG. 6 is a graph illustrating an effect of a breast image analysis method using two channel inputs.

Unlike the breast image analysis method according to the exemplary embodiment of the present invention, the AUC of the ROC curve for the convolutional neural network learning and inference result using two channel inputs was 0.772.

In contrast, when the breast image analysis method according to the exemplary embodiment of the present invention is applied, as illustrated in FIGS. 7 to 17, the AUC is 0.98 or higher.

According to the exemplary embodiment of the present invention, when four channel images are input to the convolutional neural network, the AUC value of the ROC curve was high. That is, according to the breast image analysis method according to the present invention in which the AUC value is high, it can be said that a probability that a real negative case is determined as negative and a real positive case is determined as positive is high so that the analysis performance is high.

FIG. 7 is a result obtained by setting four channel images input to the convolutional neural network in the order of a left craniocaudal view (Left CC), a left mediolateral oblique view (Left MLO), a right craniocaudal view (Right CC), and a right mediolateral oblique view (Right MLO). In this case, AUC is 0.989.

FIG. 8 is a result obtained by setting four channel images input to the convolutional neural network in the order of a left craniocaudal view (Left CC), a right craniocaudal view (Right CC), a left mediolateral oblique view (Left MLO), and a right mediolateral oblique view (Right MLO). In this case, AUC is 0.980.

FIG. 9 is a result obtained by setting four channel images input to the convolutional neural network in the order of a left mediolateral oblique view (Left MLO), a left craniocaudal view (Left CC), a right mediolateral oblique view (Right MLO), and a right craniocaudal view (Right CC). In this case, AUC is 0.995.

FIG. 10 is a result obtained by setting four channel images input to the convolutional neural network in the order of a right craniocaudal view (Right CC), a right mediolateral oblique view (Right MLO), a left craniocaudal view (Left CC), and a left mediolateral oblique view (Left MLO). In this case, AUC is 0.990.

FIG. 11 is a result obtained by setting four channel images input to the convolutional neural network in the order of a right mediolateral oblique view (Right MLO), a left mediolateral oblique view (Left MLO), a right craniocaudal view (Right CC), and a left craniocaudal view (Left CC). In this case, AUC is 0.991.

FIG. 12 is a result obtained by setting four channel images input to the convolutional neural network in the order of a right mediolateral oblique view (Right MLO), and a right craniocaudal view (Right CC), a left mediolateral oblique view (Left MLO), and a left craniocaudal view (Left CC). In this case, AUC is 0.992.

As seen from FIGS. 7 to 12, it is confirmed that the breast image analysis method according to the exemplary embodiment of the present invention shows an excellent performance similarly regardless of the order of four mammogram images.

FIG. 13 illustrates an analysis result when three breast image analysis classes are provided.

In FIGS. 6 to 12, two classes of positive or negative are classified, but in FIG. 13, an analysis result when a total of three classes of "normal", "cancer", and "benign" is classified is illustrated.

In FIG. 13, in order to draw an ROC curve for three classes, the analysis result was checked for following three cases.

1. Class 0: [normal vs cancer+benign]
2. Class 1: [cancer vs normal+benign]
3. Class 2: [benign vs normal+cancer]

In the meantime, a macro-average ROC curve means an ROC means for three cases.

As seen from FIG. 13, in all the three cases, AUC was sequentially 0.991, 0.975, and 0.991. That is, according to the breast image analysis method according to the exemplary embodiment of the present invention, it is confirmed that the analysis performance is excellent even for three cases.

It will be appreciated that various exemplary embodiments of the present invention have been described herein for purposes of illustration, and that various modifications, changes, and substitutions may be made by those skilled in the art without departing from the scope and spirit of the present invention. Therefore, the exemplary embodiments of the present invention are provided for illustrative purposes only but not intended to limit the technical concept of the present invention. The scope of the technical concept of the present invention is not limited thereto. The protective scope of the present invention should be construed based on the following claims, and all the technical concepts in the equivalent scope thereof should be construed as falling within the scope of the present invention.

The invention claimed is:

1. A breast image analysis system, comprising:
   an image receiving unit which receives four mammogram images;
   an image size adjusting unit which adjusts a size of the mammogram image received from the image receiving unit;
   a preprocessing unit which performs preprocessing on the mammogram image adjusted by the image size adjusting unit;
   a convolutional neural network (CNN)-based CNN learning unit which generates learning information by learning the image preprocessed by the preprocessing unit; and
   a CNN inference unit which receives the learning information learned from the CNN learning unit and a mammogram image to be classified from the image receiving unit to diagnose a breast abnormality,
   wherein the mammogram image to be classified which is received by the CNN inference unit has an image size which is adjusted by the size adjusting unit and the mammogram image is preprocessed by the preprocessing unit, and
   wherein the image size adjusting unit changes an angle with respect to a mediolateral oblique view image and cuts only a breast side image with respect to a pectoral muscle parallel line which is parallel to a pectoral muscle line represented in the mediolateral oblique view image and has a predetermined interval toward a nipple direction from the pectoral muscle line to be adjusted in a form of a craniocaudal (CC) view.

2. The breast image analysis system according to claim 1, wherein four mammogram images include a right craniocaudal (CC) view, a left craniocaudal (CC) view, a right mediolateral oblique (MLO) view, and a left mediolateral oblique (MLO) view.

3. The breast image analysis system according to claim 1, wherein the pectoral muscle parallel line passes through a point at which a breast in a lower side of the nipple meets at a boundary of the mediolateral oblique view image.

4. A breast image analysis method, comprising:
   (a) a step of receiving four mammogram images;
   (b) a step of adjusting sizes of the received mammogram images;
   (c) a step of preprocessing the adjusted mammogram images;
   (d) a step of generating learning information by learning the preprocessed mammogram images based on a convolutional neural network (CNN);
   (e) a step of receiving a mammogram image to be classified to classify whether a breast disease is present; and
   (f) a step of receiving the learning information learned based on the convolutional neural network (CNN) and the mammogram image to be classified to diagnose a breast abnormality,
   wherein in the step (b) of adjusting sizes of the received mammogram images, an angle with respect to a mediolateral oblique view image is changed and only a breast side image is cut with respect to a pectoral muscle parallel line which is parallel to a pectoral muscle line represented in the mediolateral oblique view image and has a predetermined interval toward a nipple direction from the pectoral muscle line to be adjusted in a form of a craniocaudal (CC) view.

5. The breast image analysis method according to claim 4, wherein the step (e) of receiving a mammogram image to be classified to classify whether a breast disease is present further includes:
   a step of adjusting a size of an image and a step of performing preprocessing on the adjusted mammogram image.

6. The breast image analysis method according to claim 4, wherein four mammogram images include a right craniocaudal (CC) view, a left craniocaudal (CC) view, a right mediolateral oblique (MLO) view, and a left mediolateral oblique (MLO) view.

7. The breast image analysis method according to claim 4, wherein the pectoral muscle parallel line passes through a point at which a breast in a lower side of the nipple meets at a boundary of the mediolateral oblique view image.

* * * * *